United States Patent [19]

Michel et al.

[11] Patent Number: 4,642,309
[45] Date of Patent: Feb. 10, 1987

[54] INDOLIN-2-ONE DERIVATIVES PREPARATION THEREOF AND INTERMEDIATES FOR THE PREPARATION THEREOF

[75] Inventors: Helmut Michel, Mannheim; Klaus Marzenell, Ladenburg; Wolfgang Kampe, Heddesheim; Wolfgang Bartsch, Viernheim; Wolfgang Schaumann, Heidelberg, all of Fed. Rep. of Germany

[73] Assignee: Boehringer Mannheim GmbH, Mannheim, Fed. Rep. of Germany

[21] Appl. No.: 780,704

[22] Filed: Sep. 26, 1985

Related U.S. Application Data

[63] Continuation of Ser. No. 592,616, Mar. 23, 1984, abandoned.

[30] Foreign Application Priority Data

Mar. 23, 1983 [DE] Fed. Rep. of Germany ....... 3310891

[51] Int. Cl.[4] .................... C07D 209/34; A61K 31/40
[52] U.S. Cl. .................... 514/269; 548/262; 548/309; 548/318; 548/336; 548/374; 548/467; 548/469; 548/486; 546/273; 544/310; 544/318; 514/339; 514/359; 514/383; 514/397; 514/414; 514/418
[58] Field of Search ............ 548/469, 467, 374, 336, 548/202, 318, 309, 486; 546/275, 26; 514/269, 339, 359, 383, 397, 414, 418; 544/310, 318

[56] References Cited

U.S. PATENT DOCUMENTS

| | | | |
|---|---|---|---|
| 3,825,558 | 7/1974 | Seeman | 548/467 |
| 3,882,143 | 5/1975 | Seeman | 548/467 |
| 3,965,095 | 6/1976 | Seeman | 548/467 |
| 4,070,470 | 1/1978 | Nakagawa et al. | 548/467 |
| 4,080,463 | 3/1978 | Troxler | 548/467 |
| 4,235,919 | 11/1980 | Berthold | 548/467 |
| 4,346,093 | 8/1982 | Friebe et al. | 546/273 |

*Primary Examiner*—George F. Lesmes
*Assistant Examiner*—S. A. Gibson
*Attorney, Agent, or Firm*—Felfe & Lynch

[57] ABSTRACT

The present invention provides indolin-2-one derivatives of the general formula:

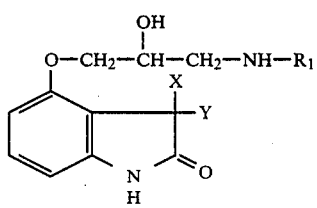

(I)

wherein $R_1$ is a $C_1$-$C_6$ alkyl radical or a radical of the general formula:

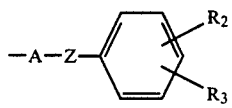

in which A is a straight-chained or branched $C_2$-$C_4$ alkylene radical and Z is an oxygen or sulphur atom, $R_2$ and $R_3$, which can be the same or different, are hydrogen or halogen atoms, hydroxyl groups, $C_2$-$C_6$ alkanoyl radicals, $C_2$-$C_4$ alkenyl radicals, $C_2$-$C_4$ alkynyl radicals, $C_1$-$C_6$ alkyl radicals, $C_1$-$C_6$ alkoxy radicals, $C_2$-$C_4$ alkenyloxy radicals, $C_2$-$C_4$ alkynyloxy radicals, $C_1$-$C_6$ alkylthio radicals, $C_2$-$C_6$ alkanoylamido radicals or radicals of the general formula:

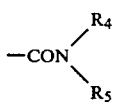

in which $R_4$ and $R_5$, which can be the same or different, are hydrogen atoms, $C_1$-$C_6$ alkyl radicals or $C_3$-$C_{10}$ cycloalkyl radicals or $R_4$ and $R_5$ together represent a $C_2$-$C_8$ alkylene radical optionally interrupted by an oxygen or sulphur atom or by an $>N-R_6$ group, in which $R_6$ is a hydrogen atom or a $C_1$-$C_6$ alkyl radical, X is a hydrogen atom, Y is a hydrogen atom or a group of the general formula

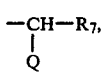

in which Q is a hydrogen atom or, together with X, can also represent a bond and $R_7$ is a heterocyclic radical which is optionally substituted one or more times by hydroxyl or $C_1$-$C_6$ alkyl or is a phenyl radical which is optionally substituted one or more times by halogen, hydroxyl, mercapto, carboxyl, $C_1$-$C_6$ alkoxycarbonyl, $C_1$-$C_6$ alkyl, $C_1$-$C_6$ alkoxy, $C_1$-$C_6$ alkylthio, $C_1$-$C_6$ alkylsulphinyl, $C_114$ $C_6$ alkylsulphonyl, $C_2$-$C_6$ alkanoylamido, $C_1$-$C_6$ alkylsulphonylamido, methylenedioxy, nitro, cyano or amino, with the proviso that $R_1$ cannot be a $C_1$-$C_6$ alkyl radical when X and Y are both hydrogen atoms; as well as the pharmacologically acceptable salts thereof.

The present invention also provides intermediates of the general formula:

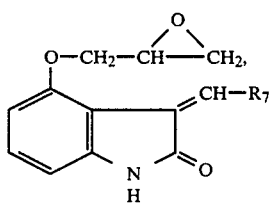

(V)

in which $R_7$ is a heterocyclic radical which is optionally (Abstract continued on next page.)

substituted one or more times by hydroxy or $C_1$–$C_6$ alkyl or is a phenyl radical which is optionally substituted one or more times by hydroxyl, halogen, mercapto, carboxyl, $C_1$–$C_6$ alkoxycarbonyl, $C_1$–$C_6$ alkyl, $C_1$–$C_6$ alkoxy, $C_1$–$C_6$ alkylthio, $C_1$14 $C_6$ alkylsulphinyl, cyano $C_1$–$C_6$ alkylsulphonyl, $C_2$–$C_6$ alkanoylamido, $C_1$–$C_6$ alkylsulphonylamido, nitro amino or methylenedioxy.

Furthermore, the invention provides processes for the preparation of the above indolin-2-one derivatives and the above intermediates, as well as pharmaceutical compositions containing the above indolin-2-one derivatives.

21 Claims, No Drawings

INDOLIN-2-ONE DERIVATIVES PREPARATION THEREOF AND INTERMEDIATES FOR THE PREPARATION THEREOF

This application is a continuation, of application Ser. No. 592,616, filed Mar. 23, 1984 now abn.

The present invention is concerned with new indolin-2-one derivatives, with the preparation thereof, with pharmaceutical compositions containing them and with intermediates for the preparation thereof.

The new indolin-2-one derivatives according to the present invention are compounds of the general formula:

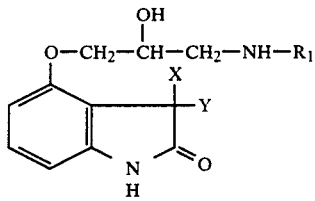

wherein $R_1$ is a $C_1-C_6$ alkyl radical or a radical of the general formula:

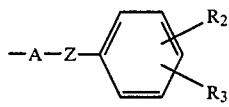

in which A is a straight-chained or branched $C_2-C_4$ alkylene group and Z is an oxygen or sulphur atom, $R_2$ and $R_3$, which can be the same or different, are hydrogen or halogen atoms, hydroxyl groups, $C_2-C_6$ alkanoyl radicals, $C_2-C_4$ alkenyl radicals, $C_2-C_4$ alkynyl radicals, $C_1-C_6$ alkyl radicals, $C_1-C_6$ alkoxy radicals, $C_2-C_4$ alkenyloxy radicals, $C_2-C_4$ alkynyloxy radicals, $C_1-C_6$ alkylthio radicals, $C_2-C_6$ alkanoylamido radicals or a radical of the general formula:

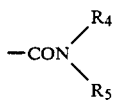

in which $R_4$ and $R_5$, which can be the same or different, are hydrogen atoms, $C_1-C_6$ alkyl or $C_3-C_{10}$ cycloalkyl radicals or $R_4$ and $R_5$ together represent a $C_2-C_8$ alkylene radical which can be interrupted by an oxygen or sulphur atom or by an $>N-R_6$ group, in which $R_6$ is a hydrogen atom or a $C_1-C_6$ alkyl radical, X is a hydrogen atom and Y is a hydrogen atom or a group of the general formula

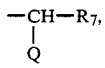

in which Q is a hydrogen atom or also, together with X, can form a bond and $R_7$ is a heterocyclic radical which is optionally substituted one or more times by hydroxyl or $C_1-C_6$ alkyl or is a phenyl radical which is optionally substituted one or more times by hydroxyl, cyano mercapto, carboxyl, $C_1-C_6$ alkoxycarbonyl, $C_1-C_6$ alkyl, $C_1-C_6$ alkoxy, $C_1-C_6$ alkylthio, $C_1-C_6$ alkylsulphinyl, $C_1-C_6$ alkylsulphonyl, $C_2-C_6$ alkanoylamido, $C_1-C_6$ alkylsulphonylamido, halogen, methylenedioxy, nitro or amino; with the proviso that $R_1$ cannot be a $C_1-C_6$ alkyl radical when X and Y are both hydrogen atoms; as well as the pharmacologically acceptable salts thereof.

Since the compounds of general formula (I) either possess an asymmetrical carbon atom or, when Y is

and X and Q are hydrogen atoms, also two asymmetrical carbon atoms, the present invention also includes the optionally-active forms and the racemic mixtures of these compounds.

For the case in which, in compounds of general formula (I), X and Q together signify a bond, the E- and Z-isomers are also included within the scope of the present invention.

Federal Republic of Germany Patent Specification No. 22 30 426 describes indolin-2-one derivatives with a similar structure to which is ascribed a blocking action on the adrenergic β-receptors. In contradistinction thereto, the compounds according to the present invention display a surprising additional activity, namely, an acute lowering of the arterial blood pressure, as well as a preferential blockade of the cardiac β-receptors. Therefore, they are especially suitable for the treatment or prophylaxis of heart and circulatory diseases, as well as of high blood pressure.

The $C_1-C_6$ alkyl radicals of the substituents $R_1$, $R_2$, $R_3$, $R_4$, $R_5$, $R_6$ and $R_7$ are straight-chained or branched radicals, for example methyl, ethyl, n-propyl, isopropyl, n-butyl, isobutyl, tert.-butyl or n-hexyl radicals, the methyl, ethyl, isopropyl and tert.-butyl radicals being especially preferred.

The cycloalkyl radicals of the substituents $R_4$ and $R_5$ are preferably cyclopropyl, cyclopentyl and cyclohexyl radicals.

The $C_2-C_6$ alkanoyl radicals of the substituents $R_2$ and $R_3$ are to be understood to be straight-chained radicals with 2 to 6 carbon atoms, the acetyl radical being preferred.

Of the $C_2-C_4$ alkenyl and alkynyl radicals of the substituents $R_2$ and $R_3$, the allyl and propargyl radicals are preferred.

The $C_1-C_6$ alkoxy and alkoxycarbonyl radicals of the substituents $R_2$, $R_3$ and $R_7$ preferably contain 1 to 4 carbon atoms, for example methoxy, ethoxy, propoxy and butoxy radicals.

Of the $C_2-C_4$ alkenyloxy and alkynyloxy radicals of the substituents $R_2$ and $R_3$, the allyloxy and propargyloxy radicals are preferred.

Of the $C_1-C_6$ alkylthio radicals of the substituents $R_2$, $R_3$ and $R_7$, the methylthio radical is preferred.

Of the $C_1-C_6$ alkylsulphonyl, alkylsulphinyl and alkylsulphonylamido radicals of the substituent $R_7$, the methylsulphonyl-, methylsulphinyl- and methylsulphonamido radicals are preferred.

By a $C_2-C_6$ alkanoylamido radical, there is preferably to be understood the acetamido radical.

By $C_2-C_8$ alkylene radicals of the substituents $R_4$ and $R_5$, there are to be understood straight-chained or branched radicals with preferably 2 to 5 carbon atoms, for example, the ethylene, propylene, n-butylene and n-pentylene radicals. Together with the nitrogen atom to which they are attached, there can be formed heterocycles, such as aziridine, azetidine, pyrrolidine, piperidine, morpholine and piperazine.

By halogen, within the meaning of the present invention, there are to be understood flourine, chlorine, bromine and iodine, fluorine, chlorine and bromine being preferred.

By heterocyclic radicals $R_7$, according to the present invention there are to be understood mono- and bicyclic radicals with one or more heteroatoms, the furan, thiophene, pyrrole, pyrazole, imidazole, triazole, tetrazole, imidazolinone, pyridine, pyrimidine, uracil, indole and indazole radicals being preferred.

The preparation of the compounds of general formula (I) according to the present invention is characterised in that, in known manner, either (a) a compound of the general formula:

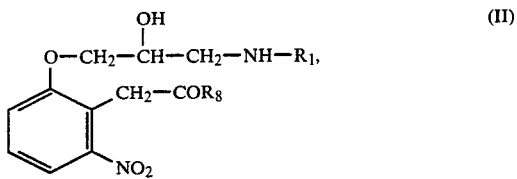

in which $R_1$ has the same meaning as above and $R_8$ is a group which can be split off, is reduced and cyclised and, if desired, reacted with a compound of the general formula:

in which $R_7$ has the same meaning as above, or with a reactive derivative thereof; or (b) a compound of the general formula:

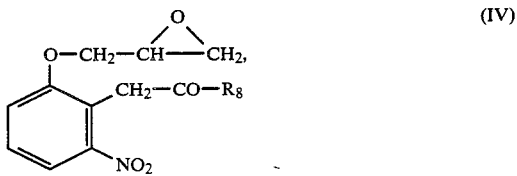

in which $R_8$ has the same meaning as above, is reduced and cyclised, if desired reacted with a compound of general formula (III) and the compound thereby obtained of the general formula:

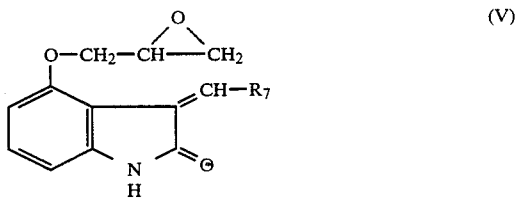

in which $R_7$ has the same meaning as above, is reacted with a compound of the general formula:

in which $R_1$ has the same meaning as above, subsequently, if desired, a compound of general formula (I), in which X and Q form a bond, is converted according to known methods into a compound of general formula (I), in which X and Q are hydrogen atoms, and, if desired, the product obtained is converted into a pharmacologically acceptable salt.

The reductions according to processes (a) and (b) can be carried out with catalytically activated hydrogen. Palladium/charcoal or Raney nickel in methanol are preferably used, operating at a temperature of from 0° to 100° C. The cyclisation takes place in an acidic medium and preferably in acetic acid solution.

The conversion of compounds of general formula (I), in which X and Q together form a bond, into compounds of general formula (I), in which X and Q are hydrogen atoms, preferably takes place by catalytic hydrogenation with hydrogen in the presence of a noble metal catalyst, for example palladium/charcoal, platinum oxide or the like, in a solvent, such as methanol or ethanol, with the addition of triethylamine.

Groups $R_8$ which can be split off and are present in compounds of general formulae (II) and (IV) are amino, imidazolyl, hydroxyl or $C_1$-$C_4$ alkoxyl radicals and preferably hydroxyl, methoxy, ethoxy or propoxy radicals.

Compounds of general formula (II) can be obtained by reacting compounds of general formula (IV) with compounds of general formula (VI). When $R_1$ is not a $C_1$-$C_6$ alkyl radical, they are new.

The preparation of compounds of general formula (IV) is described in European Patent Specification No. 00 14 928.

The compounds of general formula (V) are also new. Consequently, the present invention also includes within its scope the new intermediates of general formula (V) for the preparation of compounds of general formula (I).

The reactions of the precursors with compounds of general formula (III) can be carried out without the use of a solvent or in an inert solvent, for example, methanol, ethanol, n-butanol, diethyl ether, methylene chloride, toluene, ethyl acetate, tetrahydrofuran, dioxane, dimethylformamide or dimethyl sulphoxide, with the addition of an appropriate catalyst, for example ammonia, triethylamine, N-ethyldiisopropylamine, tributylamine, piperidine, morpholine, 1-methylpiperidine, 4-methylmorpholine or sodium methylate. Especially preferred are, however, methanol, ethanol and dimethyl sulphoxide, as well as triethylamine, piperidine and 1-methylpiperidine.

The compounds of general formula (I) according to the present invention can be obtained in the form of a racemic mixture. The separation of the racemate into the optically-active forms takes place by means of known methods via the diastereomeric salts of active acids, for example tartaric acid, malic acid or camphorsulphonic acid.

For the conversion of compounds of general formula (I) into their pharmacologically acceptable salts, they are reacted, preferably in an organic solvent, with an equivalent amount of an inorganic or organic acid, for example hydrochloric acid, hydrobromic acid, phosphoric acid, sulphuric acid, acetic acid, citric acid, tartaric acid, maleic acid, fumaric acid, benzoic acid or cyclohexylsulphaminic acid.

For the preparation of pharmaceuticals, the compounds of general formula (I) are mixed in known manner with appropriate pharmaceutical carrier substances, aroma, flavouring and colouring materials and formed, for example, into tablets or dragees or, with the addition of appropriate adjuvants, suspended or dissolved in water or an oil, for example olive oil.

The new compounds of general formula (I) according to the present invention and the salts thereof can be administered enterally or parenterally in liquid or solid form. As injection medium, it is preferred to use water which contains the additives conventionally used for injection solutions, such as stabilising agents, solubilising agents and buffers.

Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

Preferred compounds according to the present invention are, apart from the compounds mentioned in the Examples, also the following compounds:

4-{2-hydroxy-3-[2-(3-carbamoyl-4-hydroxyphenyl)-ethylamino]-propoxy}-3-(2-hydroxybenzylidene)-indolin-2-one 4-{2-hydroxy-3-[2-(3-carbamoyl-4-hydroxyphenoxy)-ethylamino]-propoxy}-3-(pyrazol-5-yl)-methyleneindolin-2-one 4-[2-hydroxy-3-(2-phenoxyethylamino)-propoxy]-3-(imidazol-5-yl)-methyleneindolin-2-one 4-[2-hydroxy-3-(2-phenoxyethylamino)-propoxy]-3-(4-methylimidazolin-2-on-5-yl)-methyleneindolin-2-one 4-{2-hydroxy-3-[2-(4-N-methylcarbamoylphenoxy)-ethylamino]-propoxy}-3-(pyrazol-5-yl)-methyleneindolin-2-one 4-{2-hydroxy-3-[2-(4-N-n-butylcarbamoylphenoxy)-ethylamino]-propoxy}-3-(pyrazol-5-yl)-methyleneindolin-2-one 4-{2-hydroxy-3-[2-(4-morpholinocarbonylphenoxy)-ethylamino]-propoxy}-3-(pyrazol-5-yl)-methyleneindolin-2-one 4-{2-hydroxy-3-[2-(4-N-methylpiperazinocarbonylphenoxy)-ethylamino]-propoxy}-3-(pyrazol-5-yl)-methyleneindolin-2-one 4-[2-hydroxy-3-(2-phenoxyethylamino)-propoxy]-3-(2-mercaptobenzylidene)-indolin-2-one 4-[2-hydroxy-3-(4-phenoxybutylamino)-propoxy]-3-(pyrazol-5-yl)-methyleneindolin-2-one 4-[2-hydroxy-3-(1,1-dimethyl-2-phenoxyethylamino)-propoxy]-3-pyrazol-5-yl)-methyleneindolin-2-one 4-{2-hydroxy-3-[2-(2-methoxyphenylmercapto)-ethylamino]-propoxy}-3-(pyrazol-5-yl)-methyleneindol-2-one.

4-<2-Hydroxy-3-[2-(4-hydroxy-phenoxy)ethylamino]-propoxy>-3-(3-chlor-benzyliden)indolin-2-one 4-<2-Hydroxy-3-[2-(4-hydroxy-phenoxy)ethylamino]-propoxy>-3-(2-methyl-benzyliden)indolin-2-one 4-<2-Hydroxy-3-[2-(4-hydroxy-phenoxy)ethylamino]-propoxy>-3-(3,4-methylendioxy-benzyliden)indolin-2-one 4-<2-Hydroxy-3-[2-(4-hydroxy-phenoxy)ethylamino]-propoxy>-3-(4-cyano-benzyliden)indolin-2-one Intermediates according to the present invention, which are obtained by reacting 4-(2,3-epoxypropoxy)-indolin-2-ones with appropriate aldehydes, include the following:

4-(2,3-epoxy-propoxy)-3-(3-chlorbenzylidene)indolin-2-one 4-(2,3-epoxy-propoxy)-3-(2-methylbenzylidene)indolin-2-one 4-(2,3-epoxy-propoxy)-3-(3,4-methylenedioxybenzylidene)indolin-2-one 4-(2,3-epoxy-propoxy)-3-(4-cyanobenzylidene)indolin-2-one 4-(2,3-epoxypropoxy)-3-(imidazol-5-yl)-methyleneindolin-2-one 4-(2,3-epoxypropoxy)-3-(1,2,4-triazol-3-yl)-methyleneindolin-2-one 4-(2,3-epoxypropoxy)-3-(4-methylimidazolin-2-on-5-yl)methyleneindolin-2-one 4-(2,3-epoxypropoxy)-3-benzylideneindolin-2-one 4-(2,3-epoxypropoxy)-3-(4-methoxybenzylidene)indolin-2-one 4-(2,3-epoxypropoxy)-3-(3,4-dimethoxybenzylidene)indolin-2-one 4-(2,3-epoxypropoxy)-3-(2-hydroxy-4-methylthiobenzylidene)-indolin-2-one 4-(2,3-epoxypropoxy)-3-(pyrrol-2-yl)-methyleneindolin-2-one 4-(2,3-epoxypropoxy)-3-(imidazol-2-yl)-methyleneindolin-2-one 4-(2,3-epoxypropoxy)-3-(pyridyl-2-yl)-methyleneindolin-2-one 4-(2,3-epoxypropoxy)-3-(thiophen-2-yl)-methyleneindolin-2-one 4-(2,3-epoxypropoxy)-3-(2-acetamidobenzylidene)indolin-2-one 4-(2,3-epoxypropoxy)-3-(2-methanesulphonylamidobenzylidene)-indolin-2-one 4-(2,3-epoxypropoxy)-3-(2-carboxybenzylidene)indolin-2-one 4-(2,3-epoxypropoxy)-3-(indol-2-yl)-methyleneindolin-2-one 4-(2,3-epoxypropoxy)-3-(2-nitrobenzylidene)indolin-2-one 4-(2,3-epoxypropoxy)-3-(uracil-4-yl)-methyleneindolin-2-one 4-(2,3-epoxypropoxy)-3-(indazol-3-yl)-methyleneindolin-3-one 4-(2,3-epoxypropoxy)-3-(2-hydroxy-4-methylsulphinylbenzylidene)-indolin-2-one.

The following Examples are given for the purpose of illustrating the present invention:

EXAMPLE 1

4-(2-Hydroxy-3-isopropylaminopropoxy)-3-benzylideneindolin-2-one 2.5 g. 4-(2-Hydroxy-3-isopropylaminopropoxy)indolin-2-one are heated under reflux for 5 hours in 50 ml. ethanol with 5 drops of piperidine and 1.3 ml. benzaldehyde. After evaporating the solution, the residue is dissolved in dilute lactic acid and diethyl ether, the aqueous phase is rendered alkaline with potassium carbonate and, after suction filtration, the base is recrystallised from isopropanol. There are obtained 2.0 g. of 4-(2-hydroxy-3-isopropylaminopropoxy)-3-benzylideneindolin-2-one; m.p. 163°–165° C.; yield 56% of theory.

The following compounds are obtained in a manner analogous to that described in Example 1:

| | starting materials and products m.p./solvent | yield % |
|---|---|---|
| (a) | 4-(2-hydroxy-3-isopropylaminopropoxy)-3-(2-hydroxybenzylidene)-indolin-2-one 181–183° C./isopropanol from 4-(2-hydroxy-3-isopropylaminopropoxy)-indolin-2-one and salicylaldehyde | 47 |
| (b) | 4-(2-hydroxy-3-isopropylaminopropoxy)-3-(4-methoxybenzylidene)-indolin-2-one 153–156° C./ethyl acetate from 4-(2-hydroxy-3-isopropylaminopropoxy)-indolin-2-one and 4-methoxybenzaldehyde | 23 |
| (c) | 4-(2-hydroxy-3-isopropylaminopropoxy)-3-(3,4-dimethoxybenzylidene)-indolin-2-one 173–174° C./ethanol from 4-(2-hydroxy-3-isopropylaminopropoxy)-indolin-2-one and 3,4-dimethoxybenzaldehyde | 72 |
| (d) | 4-(2-hydroxy-3-isopropylaminopropoxy)-3-(2-hydroxy-4-methylthiobenzylidene)-indolin-2-one 132–133° C./ethyl acetate from 4-(2-hydroxy-3-isopropylaminopropoxy)-indolin-2-one and 2-hydroxy-4-methylthiobenzaldehyde | 41 |
| (e) | 4-(2-hydroxy-3-isopropylaminopropoxy)-3-(pyrrol-2-yl)-methyleneindolin-2-one 191–193° C./ethanol from 4-(2-hydroxy-3-isopropylaminopropoxy)-indolin-2-one and pyrrole-2-aldehyde | 60 |
| (f) | 4-(2-hydroxy-3-isopropylaminopropoxy)-3-(pyrazol-5-yl)-methyleneindolin-2-one 210–211° C./ethanol from 4-(2-hydroxy-3-isopropylaminopropoxy)-indolin-2-one and pyrazole-5-aldehyde | 64 |
| (g) | 4-(2-hydroxy-3-isopropylaminopropoxy)-3-(imidazol-2-yl)-methyleneindolin-2-one 223–225° C./methanol from 4-(2-hydroxy-3-isopropylaminopropoxy)-indolin-2-one and imidazole-2-aldehyde | 20 |
| (h) | 4-(2-hydroxy-3-isopropylaminopropoxy)-3-(pyridyl-2)-methyleneindolin-2-one benzoate 180–181° C./isopropanol from 4-(2-hydroxy-3-isopropylaminopropoxy)-indolin-2-one and pyridine-2-aldehyde | 20 |
| (i) | 4-(2-hydroxy-3-isopropylaminopropoxy)-3-(thiophen-2-yl)-methyleneindolin-2-one 180–181° C./ethanol from 4-(2-hydroxy-3-isopropylaminopropoxy)-indolin-2-one and thiophene-2-aldehyde | 48 |
| (j) | 4-(2-hydroxy-3-isopropylaminopropoxy)-3-(2-acetamidobenzylidene)-indolin-2-one 174–176° C./isopropanol from 4-(2-hydroxy-3-isopropylaminopropoxy)-indolin-2-one and 2-acetamidobenzaldehyde | 35 |
| (k) | 4-(2-hydroxy-3-isopropylaminopropoxy)-3-(2-methanesulphonylamidobenzylidene)-indolin-2-one 207–208° C./ethyl acetate from 4-(2-hydroxy-3-isopropylaminopropoxy)-indolin-2-one and 2-methanesulphonylamidobenzaldehyde | 47 |
| (l) | 4-[2-hydroxy-3-(2-phenoxyethylamino)-propoxy]-3-(2-hydroxybenzylidene)-indolin-2-one 130–132° C./ethyl acetate from 4-[2-hydroxy-3-(2-phenoxyethylamino)-propoxy]-indolin-2-one (Example 2) and salicylaldehyde | 38 |
| (m) | 4-{2-hydroxy-3-[2-(2-methoxyphenoxy)-ethylamino]-propoxy}-3-(2-hydroxy-benzylidene)-indolin-2-one 171–172° C./ethanol from 4-{2-hydroxy-3-[2-(2-methoxyphenoxy)-ethylamino]-propoxy}-indolin-2-one (Example 2a) and salicylaldehyde | 48 |
| (n) | 4-{2-hydroxy-3-[2-(2-allyloxyphenoxy)-ethylamino]-propoxy}-3-(2-hydroxy-benzylidene)-indolin-2-one 147–148° C./ethanol from 4-{2-hydroxy-3-[2-(2-allyloxyphenoxy)-ethylamino]-propoxy}-indolin-2-one (Example 3) and salicylaldehyde | 42 |
| (o) | 4-{2-hydroxy-3-[2-(2-methylthiophenoxy)-ethylamino]-propoxy}-3-(2-hydroxybenzylidene)-indolin-2-one benzoate 177° C./ethanol from 4-{2-hydroxy-3-[2-methylthiophenoxy)-ethylamino]-propoxy}-indolin-2-one (Example 3a) and salicylaldehyde | 20 |
| (p) | 4-{2-hydroxy-3-[2-(4-hydroxyphenoxy)-ethylamino]-propoxy}-3-(2-hydroxy-benzylidene)-indolin-2-one benzoate 187–188° C./isopropanol from 4-{2-hydroxy-3-[2-(4-hydroxyphenoxy)-ethylamino]-propoxy}-indolin-2-one (Example 2b) and salicylaldehyde | 42 |
| (q) | 4-[2-hydroxy-3-(2-phenoxyethylamino)-propoxy]-3-(2-carboxybenzylidene)-indolin-2-one 238–240° C./water from 4-[2-hydroxy-3-(2-phenoxyethylamino)-propoxy]-indolin-2-one (Example 2) and 2-carboxybenzaldehyde | 84 |
| (r) | 4-{2-hydroxy-3-[2-(4-hydroxyphenoxy)-ethylamino]-propoxy}-3-(2-carboxy-benzylidene)-indolin-2-one 260° C./ethanol from 4-{2-hydroxy-3-[2-(4-hydroxyphenoxy)-ethylamino]-propoxy}-indolin-2-one (Example 2b) and 2-carboxybenzaldehyde | 70 |
| (s) | 4-{2-hydroxy-3-[2-(4-hydroxyphenoxy)-ethylamino]-propoxy}-3-(2-methane-sulphonylamidobenzylidene)-indolin-2-one 153–158° C./ethyl acetate from 4-{2-hydroxy-3-[2-(4-hydroxyphenoxy)-ethylamino]-propoxy}-indolin-2-one (Example 2b) and 2-methanesulphonyl-amidobenzaldehyde | 44 |
| (t) | 4-{2-hydroxy-3-[2-(4-hydroxyphenoxy)-ethylamino]-propoxy}-3-(pyrrol-2-yl)-methyleneindolin-2-one 205° C./ethanol from 4-{2-hydroxy-3-[2-(4-hydroxyphenoxy)-ethylamino]-propoxy}-indolin-2-one (Example 2b) and pyrrole-2-aldehyde | 64 |
| (u) | 4-[2-hydroxy-3-(2-phenoxyethylamino)-propoxy]-3-(pyrazol-5-yl)-methylene-indolin-2-one 161–162° C./ethanol from 4-[2-hydroxy-3-(2-phenoxyethylamino)-propoxy]-indolin-2-one (Example 2) and | 57 |

-continued

| | starting materials and products m.p./solvent | yield % |
|---|---|---|
| (v) | pyrazole-5-aldehyde<br>4-{2-hydroxy-3-[2-(4-hydroxyphenoxy)-ethylamino]-propoxy}-3-(pyrazol-5-yl)-methyleneindolin-2-one<br>178–180° C./ethanol<br>from<br>4-{2-hydroxy-3-[2-(4-hydroxyphenoxy)-ethylamino]-propoxy}-indolin-2-one (Example 2b) and pyrazole-5-aldehyde | 64 |
| (w) | 4-[2-hydroxy-3-(2-phenoxyethylamino)-propoxy]-3-(indol-2-yl)-methylene-indolin-2-one<br>204–205° C./n-butanol<br>from<br>4-[2-hydroxy-3-(2-phenoxyethylamino)-propoxy]-indolin-2-one (Example 2) and indole-2-aldehyde | 74 |
| (x) | 4-[2-hydroxy-3-(2-phenoxyethylamino)-propoxy]-3-(2-nitrobenzylidene)-indolin-2-one<br>159–161° C./ethyl acetate<br>from<br>4-[2-hydroxy-3-(2-phenoxyethylamino)-propoxy]-indolin-2-one (Example 2) and 2-nitrobenzaldehyde | 40 |
| (y) | 4-[2-hydroxy-3-(2-phenoxyethylamino)-propoxy]-3-(uracil-4-yl)-methylene-indolin-2-one<br>216–218° C./ethyl acetate<br>from<br>4-[2-hydroxy-3-(2-phenoxyethylamino)-propoxy]-indolin-2-one (Example 2) and uracil-4-aldehyde | 46 |
| (z) | 4-[2-hydroxy-3-(2-phenoxyethylamino)-propoxy]-3-(indazol-3-yl)-methylene-indolin-2-one<br>192–194° C./ethyl acetate<br>from<br>4-[2-hydroxy-3-(2-phenoxyethylamino)-propoxy]-indolin-2-one (Example 2) and indazole-3-aldehyde | 27 |
| (z1) | 4-[2-hydroxy-3-(2-phenoxyethylamino)-propoxy]-3-(1,2,4-triazol-3-yl)-methyleneindolin-2-one<br>177–180° C./ethanol<br>from<br>4-[2-hydroxy-3-(2-phenoxyethylamino)-propoxy]-indolin-2-one (Example 2) and 1,2,4-triazole-3-aldehyde | 28 |
| (z2) | 4-{2-hydroxy-3-[2-(4-carbamoylphenoxy)-ethylamino]-propoxy}-3-(pyrazol-5-yl)-methyleneindolin-2-one<br>158–160° C./methanol<br>from<br>4-{2-hydroxy-3-[2-(4-carbamoylphenoxy)-ethylamino]-propoxy}-indolin-2-one (Example 2c) and pyrazole-5-aldehyde | 54 |
| (z3) | 4-{2-hydroxy-3-[2-(4-N—isopropyl-carbamoylphenoxy)-ethylamino]-propoxy}-3-(pyrazol-5-yl)-methyleneindolin-2-one<br>217–219° C./methanol<br>from<br>4-{2-hydroxy-3-[2-(4-N—isopropyl-carbamoylphenoxy)-ethylamino]-propoxy}-indolin-2-one (Example 2d) and pyrazole-5-aldehyde | 70 |
| (z4) | 4-{2-hydroxy-3-[2-(4-N—cyclopentyl-carbamoylphenoxy)-ethylamino]-propoxy}-3-(pyrazol-5-yl)-methylene-indolin-2-one<br>195–198° C./ethanol<br>from<br>4-{2-hydroxy-3-[2-(4-N—cyclopentyl-carbamoylphenoxy)-ethylamino]-propoxy}-indolin-2-one (Example 2e) and pyrazole-5-aldehyde | 64 |
| (z5) | 4-{2-hydroxy-3-[2-(4-N,N—dimethyl-carbamoylphenoxy)-ethylamino]-propoxy}-3-(pyrazol-5-yl)-methylene-indolin-2-one<br>128–131° C./ethanol<br>from<br>4-{2-hydroxy-3-[2-(4-N,N—dimethyl-carbamoylphenoxy)-ethylamino]-propoxy}-indolin-2-one (Example 2f) and pyrazole-5-aldehyde | 31 |
| (z6) | 4-[2-hydroxy-3-(2-phenoxyethylamino)-propoxy]-3-(2-aminobenzylidene)-indolin-2-one<br>108–112° C./ethanol<br>from<br>4-[2-hydroxy-3-(2-phenoxyethylamino)-propoxy]-indolin-2-one (Example 2) and 2-aminobenzaldehyde | 10 |
| (z7) | 4-{2-hydroxy-3-[2-(4-hydroxyphenoxy)-ethylamino]-propoxy}-3-(1,2,4-triazol-3-yl)-methyleneindolin-2-one<br>233–235° C./ethanol<br>from<br>4-{2-hydroxy-3-[2-(4-hydroxyphenoxy)-ethylamino]-propoxy}-indolin-2-one (Example 2b) and 1,2,4-triazole-3-aldehyde | 28 |

The starting materials required for the preparation of the above compounds can be prepared in the following manner:

4-(2-Hydroxy-3-isopropylaminopropoxy)-indolin-2-one 14.0 g. Ethyl 2-(2,3-epoxypropoxy)-6-nitrophenylacetate (see European Patent Specification No. 00 14 928) are dissolved in 140 ml. isopropylamine and left to stand for 3 days at ambient temperature. After removal of excess amine, the residue is dissolved in diethyl ether and dilute lactic acid, the aqueous phase is rendered alkaline with potassium carbonate and extracted with diethyl ether. After drying and evaporation, there are obtained 16 g. of a brownish oil which is immediately hydrogenated in 150 ml. methanol and 150 ml. acetic acid at ambient temperature and 1 bar hydrogen pressure over 10% palladium/charcoal. The catalyst is filtered off with suction and the filtrate is evaporated in a vacuum. The residue obtained is dissolved in water and filtered. By the addition of potassium carbonate, the base is precipitated out and then filtered off. After drying, there are obtained 10.4 g. 4-(2-hydroxy-3-isopropylaminopropoxy)-indolin-2-one; m.p. 173°–175° C.; yield 89% of theory.

The following compounds can be obtained in an analogous manner by reaction with amines and subsequent hydrogenation and cyclisation:

EXAMPLE 2

| | starting materials and products m.p./solvent | yield % |
|---|---|---|
| | 4-[2-hydroxy-3-(2-phenoxyethylamino)-propoxy]-indolin-2-one<br>143–145° C./ethyl acetate<br>from<br>ethyl 2-(2,3-epoxypropoxy)-6-nitrophenylacetate and 2-phenoxyethylamine | 75 |
| (a) | 4-{2-hydroxy-3-[2-(2-methoxyphenoxy)-ethylamino]-propoxy}-indolin-2-one<br>156–158° C./ethyl acetate<br>from<br>ethyl 2-(2,3-epoxypropoxy)-6-nitrophenylacetate and 2-(2-methoxyphenoxy)- | 89 |

| | starting materials and products m.p./solvent | yield % |
|---|---|---|
| | ethylamine | |
| (b) | 4-{2-hydroxy-3-[2-(4-hydroxyphenoxy)-ethylamino]-propoxy}-indolin-2-one 186–189° C./ethanol from ethyl 2-(2,3-epoxypropoxy)-6-nitro-phenylacetate and N—benzyl-2-(4-benzyloxyphenoxy)-ethylamine | 80 |
| (c) | 4-{2-hydroxy-3-[2-(4-carbamoylphenoxy)-ethylamino]-propoxy}-indolin-2-one 143–147° C./ethyl acetate from ethyl 2-(2,3-epoxypropoxy)-6-nitro-phenylacetate and 2-(4-carbamoyl-phenoxy)-ethylamine | 66 |
| (d) | 4-{2-hydroxy-3-[2-(4-N—isopropyl-carbamoylphenoxy)-ethylamino]-propoxy}-indolin-2-one 175–178° C./ethyl acetate from ethyl 2-(2,3-epoxypropoxy)-6-nitro-phenyl acetate and 2-(4-N—isopropyl-carbamoylphenoxy)-ethylamine | 48 |
| (e) | 4-{2-hydroxy-3-[2-(4-N—cyclopentyl-carbamoylphenoxy)-ethylamino]-propoxy}-indolin-2-one 180–184° C./ethyl acetate from ethyl 2-(2,3-epoxypropoxy)-6-nitro-phenylacetate and 2-(4-N—cyclopentyl-carbamoylphenoxy)-ethylamine | 61 |
| (f) | 4-{2-hydroxy-3-[2-(4-N,N—dimethyl-carbamoylphenoxy)-ethylamino]-propoxy}-indolin-2-one 131–134° C./ethyl acetate from ethyl 2-(2,3-epoxypropoxy)-6-nitro-phenylacetate and 2-(4-N,N—dimethyl-carbamoylphenoxy)-ethylamine | 48 |

EXAMPLE 3

4-{2-Hydroxy-3-[2-(2-allyloxyphenoxy)-ethylamino]-propoxy}-indolin-2-one 4.1 g. 4-(2,3-Epoxypropoxy)-indolin-2-one (Example 6) are dissolved in 200 ml. n-butanol, 11.6 g. 2-(2-allyloxyphenoxy)-ethylamine are added thereto and the reaction mixture is stirred for 2 days at ambient temperature. After distilling off the n-butanol, the residue is recrystallised from ethyl acetate. There are obtained 6.2 g. 4-{2-hydroxy-3-[2-(2-allyloxyphenoxy)-ethylamino]-propoxy}-indolin-2-one; m.p. 148°–149° C.; yield 77% of theory.

The following compound is obtained in a manner analogous to that described in Example 3:

| | starting materials and product m.p./solvent | yield % |
|---|---|---|
| (a) | 4-{2-hydroxy-3-[2-(2-methylthio-phenoxy)-ethylamino]-propoxy}-indolin-2-one 173–175° C./ethyl acetate from 4-(2,3-epoxypropoxy)-indolin-2-one (Example 6) and 2-(2-methylthio-phenoxy)-ethylamine | 85 |

EXAMPLE 4

4-(2-Hydroxy-3-isopropylaminopropoxy)-3-(pyrazol-5-yl)-methyleneindolin-2-one 2.8 g. 4-(2,3-Epoxypropoxy)-3-(pyrazol-5-yl)-methyleneindolin-2-one (Example 5) are stirred in 25 ml. n-butanol and 25 ml. isopropylamine for 2 days at ambient temperature. After removal of the solvent, the residue is taken up in ethyl acetate and water and filtered off with suction. After drying, there is obtained 1.9 g. 4-(2-hydroxy-3-isopropylaminopropoxy)-3-(pyrazol-5-yl)-methyleneindolin-2-one; m.p. 209°–211° C.; yield 45% of theory.

The following compound is obtained in a manner analogous to that described in Example 4:

| | starting materials and product m.p./solvent | yield % |
|---|---|---|
| (a) | 4-[2-hydroxy-3-(2-phenoxyethylamino)-propoxy]-3-(pyrazol-5-yl)-methylene-indolin-2-one 161–162° C./ethyl acetate/ethanol from 4-(2,3-epoxypropoxy)-3-(pyrazol-5-yl)-methyleneindolin-2-one (Example 5) and 2-phenoxyethylamine | 40 |

The starting material required in Example 4 can be prepared as follows:

EXAMPLE 5

4-(2,3-Epoxypropoxy)-3-(pyrazol-5-yl)-methyleneindolin-2-one 4.1 g. 4-(2,3-Epoxypropoxy)-indolin-2-one (Example 6) are dissolved in 40 ml. dimethyl sulphoxide, mixed with 2.0 g. pyrazole-5-aldehyde and 2.8 ml. trimethylamine and stirred for 2 days at ambient temperature. The reaction mixture is mixed with 150 ml. water and extracted with ethyl acetate. After drying with anhydrous sodium sulphate and evaporating, there crystallise out 3.9 g. 4-(2,3-epoxypropoxy)-3-(pyrazol-5-yl)-methyleneindolin-2-one; m.p. 229° C.; yield 68% of theory.

The following compound is obtained in an analogous manner:

| | starting materials and product m.p./solvent | yield % |
|---|---|---|
| (a) | 4-(2,3-epoxypropoxy)-3-(2-hydroxy-benzylidene)-indolin-2-one 172–174° C./ethyl acetate from 4-(2,3-epoxypropoxy)-indolin-2-one (Example 6) and salicylaldehyde | 40 |

The epoxide required for the preparation of the compounds of Examples 3, 3a, 5 and 5a can be prepared as follows:

EXAMPLE 6

4-(2,3-Epoxypropoxy)-indolin-2-one

A solution of 28.2 g. ethyl 2-(2,3-epoxypropoxy)-6-nitrophenylacetate in 300 ml. methanol is mixed with 3 ml. Raney nickel and hydrogenated at 1 bar hydrogen pressure. The catalyst is filtered off with suction and the filtrate is evaporated. The residue is dissolved in 300 ml. diethyl ether, insolubles are filtered off and the filtrate is mixed with 12 ml. acetic acid. After stirring overnight, the product is filtered off with suction and washed with diethyl ether. There are obtained 13.1 g. 4-(2,3-epoxypropoxy)-indolin-2-one; m.p. 164°–166° C.; yield 64% of theory.

EXAMPLE 7

4-(2-Hydroxy-3-isopropylaminopropoxy)-3-(2-hydroxybenzyl)-indolin-2-one benzoate 5.8 g. 4-(2-Hydroxy-3-isopropylaminopropoxy)-3-(2-hydroxybenzylidene)-indolin-2-one (Example 1a) are dissolved in 150 ml. methanol, mixed with 15 ml. triethylamine and hydrogenated at ambient temperature over 1 g. 10% palladium/charcoal at 1 bar hydrogen pressure. The catalyst is filtered off with suction, the filtrate is distilled in a vacuum, the residue is dissolved in ethyl acetate and mixed with an equivalent amount of benzoic acid. After filtering with suction, there are obtained 2.5 g. 4-(2-hydroxy-3-isopropylaminopropoxy)-3-(2-hydroxybenzyl)indolin-2-one benzoate; m.p. 198°–202° C.; yield 34% of theory.

The following compounds are obtained in a manner analogous to that described in Example 7:

| | starting materials and products m.p./solvent | yield % |
|---|---|---|
| (a) | 4-(2-hydroxy-3-isopropylaminopropoxy)-3-(3,4-dimethoxybenzyl)-indolin-2-one benzoate 82–84° C./ethyl acetate from 4-(2-hydroxy-3-isopropylaminopropoxy)-3-(3,4-dimethoxybenzylidene)-indolin-2-one (Example 1c) | 74 |
| (b) | 4-{2-hydroxy-3-[2-(2-methoxyphenoxy)-ethylamino]-propoxy}-3-(3,4-dimethoxybenzyl)-indolin-2-one oxalate 93–95° C./methanol from 4-{2-hydroxy-3-[2-(2-methoxyphenoxy)-N—benzylethylamino]-propoxy}-3-(3,4-dimethoxybenzylidene)-indolin-2-one | 50 |
| (c) | 4-{2-hydroxy-3-[2-(2-methoxyphenoxy)-ethylamino]-propoxy}-3-(2-hydroxybenzyl)-indolin-2-one oxalate 156–158° C./methanol from 4-{2-hydroxy-3-[2-(2-methoxyphenoxy)-ethylamino]-propoxy}-3-(2-hydroxybenzylidene)-indolin-2-one (Example 1m) | 50 |
| (d) | 4-{2-hydroxy-3-[2-(4-hydroxyphenoxy)-ethylamino]-propoxy}-3-(2-hydroxybenzyl)-indolin-2-one cyclohexylsulphaminate 138–141° C./ethanol from 4-{2-hydroxy-3-[2-(4-hydroxyphenoxy)-ethylamino]-propoxy}-3-(2-hydroxybenzylidene)-indolin-2-one (Example 1p) | 30 |
| (e) | 4-{2-hydroxy-3-[2-(4-hydroxyphenoxy)-ethylamino]-propoxy}-3-(pyrazol-5-yl-methyl)-indolin-2-one fumarate 60° C. sinters/isopropanol from 4-{2-hydroxy-3-[2-(4-hydroxyphenoxy)-ethylamino]-propoxy}-3-(pyrazol-5-yl)-methyleneindolin-2-one (Example 1v) | 30 |
| (f) | 4-[2-hydroxy-3-(2-phenoxyethylamino)-propoxy]-3-(pyrazol-5-yl-methyl)-indolin-2-one fumarate 85° C. sinters/isopropanol from 4-[2-hydroxy-3-(2-phenoxyethylamino)-propoxy]-3-(pyrazol-5-yl)-methylene-indolin-2-one (Example 1u) | 63 |

The starting material required for the preparation of the compound of Example 7b can be prepared as follows:

3-(3,4-Dimethoxybenzylidene)-4-{2-hydroxy-3-[2-(2-methoxyphenoxy)-N-benzylethylamino]-propoxy}indolin-2-one 4.1 g. 4-(2,3-Epoxypropoxy)-indolin-2-one (Example 6) are dissolved in 200 ml. n-butanol and 5.2 g. N-benzyl-(2-methoxyphenoxy)-ethylamine are added thereto. After 3 days, the solvent is removed in a vacuum, 11.5 g. of crude product being obtained which, for further reaction, is not purified.

11.5 g. 4-[2-Hydroxy-3-[2-(2-methoxyphenoxy)-N-benzylethylamino]-propoxy}-indolin-2-one are dissolved in 200 ml. ethanol, 4.0 g. 3,4-dimethoxybenzaldehyde and 1 ml. piperidine are added thereto and subsequently the reaction mixture is heated under reflux for 16 hours. After cooling, the product is filtered off with suction, washed with ethanol and dried. There are obtained 9.3 g. 3-(3,4-dimethoxybenzylidene)-4-{2-hydroxy-3-[2-(2-methoxyphenoxy)-N-benzylethylamino]-propoxy}indolin-2-one; m.p. 151°–155° C.; yield 76% of theory.

EXAMPLE 8

4-(2-Hydroxy-3-isopropylaminopropoxy)-3-(2-hydroxy-4-methylsulphinylbenzylidene)-indolin-2-one acetate 2.8 g. 4-(2-Hydroxy-3-isopropylaminopropoxy)-3-(2-hydroxy-4-methylthiobenzylidene)-indolin-2-one (Example 1d) are dissolved in 50 ml. acetic acid and mixed with 0.85 ml. 30% hydrogen peroxide. After stirring for 3 hours at ambient temperature, the reaction mixture is evaporated in a vacuum and the residue mixed with water. After decanting off, the oily residue is dissolved in ethanol, mixed with 0.4 ml. glacial acetic acid and the crystalline product is filtered off with suction. There are obtained 2.0 g. 4-(2-hydroxy-3-isopropylaminopropoxy)-3-(2-hydroxy-4-methylsulphinylbenzylidene)-indolin-2-one acetate; m.p. 135°–140° C.; yield 68% of theory.

A. Beta-Receptor Blocking Activity Experiments

Rabbits were fixed in wooden cages and the blood pressure derived using a catheter placed in the lateral ear artery (details as under 2.). From the blood pressure pulsations, the heart rate was digitally read using an integrator. The beta-receptor blocking quality was determined by measuring inhibitory action against 1 mcg/kg i.v. isoprenaline. The inhibition of the isoprenaline effects on the heart rate increase (beta 1-blockage) is advantageous and can be used therapeutically. From the inhibiting doses calculated over a regression for a 30 and 50%-inhibition of the isoprenaline effects, the beta-blockage was determined on the 30 and 50% levels ($ID_{30}$ and $ID_{50}$).

B. Vasodilating Activity Experiments

Rabbits were anesthetized with 26%-urethane 5 ml/kg i.v. For a continual measurement of the arterial blood pressure a catheter was implanted into the Arteria femoralis. The blood pressure was measured by means of an electromechanical pressure transducer (Statham P 23/Db). The impulses were registered on a direct printer and after calibration evaluated with a mercury manometer. After determining the starting value, both carotid arteries (Aa. carotides) were occluded for 2 min and thereby the blood pressure temporarily raised (Carotis-Sinus-Relief Reflex-CSE). Following that, the substances were injected in increasing doses and 8 min. later the CSE reflex induced again. In periods of 15 min each, in logarithmically rising dosage (factor 2), the test substance was injected again and the CSE value induced again. Substances which under these conditions weaken the rise of the blood pressure under CSE can be regarded as vasodilating. To estimate the blood pressure lowering quality, the dose was calculated which weakens the CSE reflex by 30 mm Hg (ED-30 mm Hg).

Evaluation

The products of the invention were tested for comparison with the known conventional beta-blocker propranolol (marketed as dociton) and Sandoz substances BM 12.946 and BM 14.171). (Ex. 10 and Ex. 1 from
Propranolol = 1-(isopropylamino)-3-(1-naphthyloxy)-2-propanol
BM  12.946 = 4-<2-hydroxy-3-[2-(4-methoxyphenyl)ethylamino]propoxy>oxindol
BM  14.171 = 4-(2-hydroxy-3-isopropylaminopropoxy)oxindol German No. OS 22 30 426). The results of this testing is shown in the Table below.

While the reference substances BM 12.946, BM 14.171 and propranolol are potent beta-blockers, they do not have or at least do not have any relevantly vasodilating quality ($ED_{-30}$ greater than 9 mg/kg i.v.). Higher doses of propranolol than 10 mg/kg i.v. are poorly, tolerated those over 30 mg/kg i.v. are not tolerated at all.

| Example No. | Substance | $\beta_1$-Blockade mcg/kg i.v. | | Vasodilatation CSE | BQ $ID_{50}$ fcor |
|---|---|---|---|---|---|
| | | $ID_{30}$ fcor | $ID_{50}$ fcor | $ED_{-30}$ mcg/kg i.v. | $ED_{-30}$ mm Hg |
| | Propranolol | 126 | 331 | 30000 | 0,01 |
| | BM 12.946 | 46 | 188 | 9130 | 0,02 |
| | BM 14.171 | 1,2 | 4,3 | 11600 | 0,0004 |
| (1a) | BM 12.746 | 98 | 317 | 2710 | 0,12 |
| (1p) | BM 12.816 | 192 | 932 | 750 | 1,24 |
| (7d) | BM 12.819 | 27 | 85 | 970 | 0,09 |
| (1d) | BM 12.823 | 21 | 46 | 1480 | 0,03 |
| (1r) | BM 12.828 | 205 | 823 | 2030 | 0,41 |
| (1u) | BM 12.838 | 9,9 | 58 | 331 | 0,18 |
| (7f) | BM 12.842 | 334 | 1020 | 430 | 2,37 |
| (7e) | BM 12.843 | 65 | 254 | 540 | 0,47 |

The results indicate that the inventive compounds balance vaso dilating and beta-blocking activity to a much greater extent than do the prior art materials.

In actual administration of the inventive compounds, e.g., in the treatment of hypertension or angina pectoris, the appropriate dosage is of course dependent on the condition of the patient and the specific infirmity to be treated. In general, treatment should begin with small doses (e.g., 100 mg) and increased gradually depending upon the patient's response. The dosage can be increased at 5 to 7 day intervals until an average daily dosage of 100 to 300 mg is reached. For maintenance, 2 to 4 doses a day are usually required. These dosage levels will generally be appropriate, both for achieving a vaso dilating effect, i.e., for reducing blood pressure, and for inhibition of adrenergic beta-receptor activity.

The present invention provides pharmaceutical compositions which contain at least one of the new compounds in admixture with a solid or liquid pharmaceutial diluent or carrier and, if desired, also with odoriferous, flavoring and/or coloring materials, followed by forming into, for example, tablets or dragees or, with the addition of appropriate adjuvants, suspended or dissolved in water or oil, for example, olive oil.

It will be understood that the specification and examples are illustrative but not limitative of the present invention and that other embodiments within the spirit and scope of the invention will suggest themselves to those skilled in the art.

What is claimed is:

1. An indolin-2-one compound of the formula I as follows:

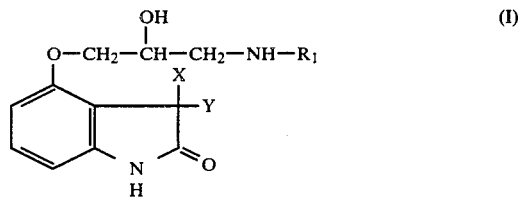

wherein $R_1$ is a $C_1$–$C_6$ alkyl, or a group of the formula

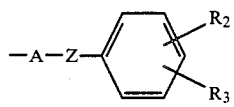

wherein A is a straight-chained or branched $C_2$–$C_4$ alkylene and z is oxygen,
$R_2$ is hydrogen, hydroxyl, $C_1$–$C_6$ alkoxy or $C_2$–$C_4$ alkenyloxy,
$R_3$ is hydrogen
X is hydrogen
Y is hydrogen, or a group of the general formula

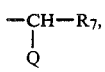

wherein Q is hydrogen or Q and X together represent a bond, and $R_7$ is imidazole, triazole, pyrrole, pyrazole, pyridine, thiophene, indole, indazole, or uracil or $R_7$ is phenyl which is optionally substituted one or two times by hydroxyl, carboxyl, $C_1$–$C_6$ alkoxy, $C_1$–$C_6$ alkylthio, $C_1$–$C_6$ alkylsulphinyl, $C_1$–$C_6$ alkylsulphonylamido, methylenedioxy, nitro, or amino,
with the proviso that $R_1$ cannot be a $C_1$–$C_6$ alkyl radical when X and Y are both hydrogen atoms; or the pharmacologically acceptable salts thereof.

2. The compound of claim 1, wherein $R_1$ is a $C_1$-$C_6$ alkyl radical and X and Q together represent a bond.

3. The compound of claim 1 wherein Q and X together represent a bond and $R_7$ is phenyl substituted one or two times by hydroxyl, carboxyl, $C_1$-$C_6$ alkoxy, $C_1$-$C_6$ alkylthio, $C_1$-$C_6$ alkylsulphinyl, $C_2$-$C_6$ alkanoylamido, $C_1$-$C_6$ alkylsulphonylamido, nitro or amino.

4. The compound of claim 1, wherein $R_1$ is the group of the general formula

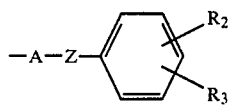

wherein
A is ethylene,
Z is oxygen,
$R_2$ is hydrogen, hydroxyl, $C_1$-$C_6$ alkoxy or $C_2$-$C_4$ alkenyloxy.

5. The compound of claim 4 wherein $R_2$ is hydroxyl.
6. The compound of claim 4 wherein $R_2$ is hydrogen.
7. The compound as claimed in claim 1 designated 4-(2-hydroxy-3-isopropylaminopropoxy)-3-(2-hydroxybenzylidene)-indolin-2-one.
8. The compound as claimed in claim 1 designated 4-(2-hydroxy-3-isopropylaminopropoxy)-3-(2-hydroxy-4-methylthiobenzylidene)-indolin-2-one and the pharmacologically acceptable salts thereof.
9. The compound as claimed in claim 1 designated 4-{2-hydroxy-3-[2-(4-hydroxyphenoxy)ethylamino]-propoxy}-3-(2-hydroxybenzylidene)-indolin-2-one and the pharmacologically acceptable salts thereof.
10. The compound as claimed in claim 1 designated 4-{2-hydroxy-3-[2-(4-hydroxyphenoxy)ethylamino]-propoxy}-3-(2-carboxybenzylidene)-indolin-2-one and the pharmacologically acceptable salts thereof.
11. The compound as claimed in claim 1 designated 4-[2-hydroxy-3-(2-phenoxyethylamino)propoxy]-3-(pyrazol-5-yl)-methyleneindolin-2-one and the pharmacologically acceptable salts thereof.
12. The compound as claimed in claim 1 designated 4-{2-hydroxy-3-[2-(4-hydroxyphenoxy)ethylamino]-propoxy}-3-(2-hydroxybenzyl)-indolin-2-one and the pharmacologically acceptable salts thereof.
13. The compound as claimed in claim 1 designated 4-{2-hydroxy-3-[2-(4-hydroxyphenoxy)ethylamino]-propoxy}-3-(pyrazol-5-yl-methyl)-indolin-2-one and the pharmacologically acceptable salts thereof.
14. The compound as claimed in claim 1 designated 4-[2-hydroxy-3-(2-phenoxyethylamino)propoxy]-3-(pyrazol-5-yl-methyl)indolin-2-one and the pharmacologically acceptable salts thereof.
15. A pharmaceutical composition for the treatment of circulatory and cardiac diseases comprising a pharmaceutically acceptable carrier and in effective amounts, an indolin-2-one derivative compound as claimed in claim 1.
16. A method of treating a subject for circulatory and cardiac diseases which comprises administering to such subject an effective amount of an indolin-2-one derivative compound as claimed in claim 1.
17. The method as claimed in claim 13 wherein said disease is hypertension.
18. The method as claimed in claim 13 wherein said disease is angina pectoris.
19. The compound as claimed in claim 1 designated 4-[2-hydroxy-3-(2-phenoxyethylamino)-propoxy]-indolin-2-one.
20. The compound of claim 4 wherein X=Y=hydrogen $R_2$ is hydrogen or hydroxy.
21. The compound of claim 1 wherein Y is a group of the general formula

wherein Q is hydrogen or Q and X together represent a bond, and $R_7$ is imidazole, triazole, pyrrole, pyrazole, pyridine, thiophene, indole, indazole, or uracil or $R_7$ is phenyl or phenyl substituted one or two times by hydroxyl, carboxyl, $C_1$-$C_6$ alkoxy, $C_1$-$C_6$ alkylthio, $C_1$-$C_6$ alkylsulphinyl, $C_1$-$C_6$ alkylsulphonylamido, nitro, or amino.

* * * * *

UNITED STATES PATENT AND TRADEMARK OFFICE
CERTIFICATE OF CORRECTION

PATENT NO. : 4,642,309
DATED : February 10, 1987
INVENTOR(S) : Helmut Michel et al.

It is certified that error appears in the above-identified patent and that said Letters Patent is hereby corrected as shown below:

Col. 2, line 14, "optionally-active" should read -- optically-active --;

Col. 5, line 25, "hydroxyphenyl" should read -- hydroxyphenoxy --;

Col. 16, line 32, "oxygen," should read -- oxygen or sulphur; --

Col. 18, line 22, "13" should read -- 16 --
     line 24, "13" should read -- 16 --

Abstract, page 1,
Col. 2, line 25, "$C_1 14 C_6$" should read -- $C_1$-$C_6$ --

Abstract, page 2,
Col. 1, line 5, "$C_1 14 C_6$" should read -- $C_1$-$C_6$ --

Signed and Sealed this

Seventeenth Day of November, 1987

*Attest:*

DONALD J. QUIGG

*Attesting Officer*    *Commissioner of Patents and Trademarks*